United States Patent [19]
Sanderson et al.

[11] Patent Number: 5,792,779
[45] Date of Patent: Aug. 11, 1998

[54] PYRIDINONE THROMBIN INHIBITORS

[75] Inventors: Philip E. Sanderson, Philadelphia; Terry A. Lyle, Lederach; Joseph P. Vacca, Telford; William C. Lumma, Pennsburg; Stephen F. Brady, Philadelphia; Thomas J. Tucker, North Wales, all of Pa.

[73] Assignee: Merck & Co., Inc., Rahway, N.J.

[21] Appl. No.: 802,370

[22] Filed: Feb. 19, 1997

[51] Int. Cl.⁶ .............. C07D 213/64; C07D 213/75; C07D 213/70; A61K 31/44
[52] U.S. Cl. .............. 514/352; 546/291; 546/292
[58] Field of Search .................. 546/292, 291; 514/352

[56] References Cited

U.S. PATENT DOCUMENTS

| | | | |
|---|---|---|---|
| 5,260,307 | 11/1993 | Ackermann et al. | 514/323 |
| 5,405,854 | 4/1995 | Ackermann et al. | 514/315 |
| 5,510,369 | 4/1996 | Lumma et al. | 514/422 |

FOREIGN PATENT DOCUMENTS

| | | |
|---|---|---|
| 0 509 769 A2 | 10/1992 | European Pat. Off. . |
| 94/25051 | 11/1994 | WIPO . |
| 96/11697 | 4/1996 | WIPO . |
| 96/31504 | 10/1996 | WIPO . |
| 96/32110 | 10/1996 | WIPO . |
| 97/01338 | 1/1997 | WIPO . |

OTHER PUBLICATIONS

Bernstein, et al., J. Med. Chem., 37, 3313–3326 "Nonpeptidic Inhibitors of Human Leukocyte Elastase . . . .", 1994.

Brown et al., J. Med. Chem., "Design of Orally Active, Non-Peptidic Inhibitors of Human Leukocyte Elastase", vol. 37, No. 9, pp. 1259–1261 (1994).

Edwards et al., J. Am Chem. Soc., "Design, Synthesis, and Kenetic Evaluation of a Unique Class of Elastase Inhibitors . . . ", vol. 114, No. 5, pp. 1854–1863 (1992).

*Primary Examiner*—Alan L. Rotman
*Attorney, Agent, or Firm*—Richard S. Parr; Mel Winokur

[57] ABSTRACT

Compounds of the invention are useful in inhibiting thrombin and associated thrombotic occlusions and have the following structure:

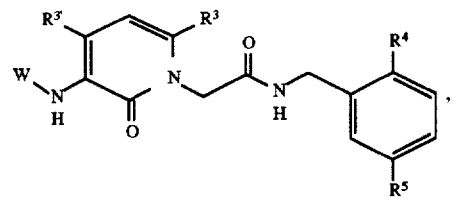

for example:

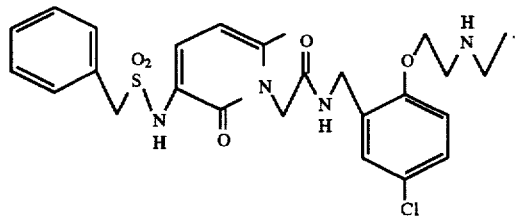

15 Claims, No Drawings

PYRIDINONE THROMBIN INHIBITORS

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl α-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or α-keto carboxyl derivatives.

R. J. Brown et al., *J. Med. Chem.*, Vol., 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol.9, pages 73–86 (1995) describes rigid amidino-phenylalanine thrombin inhibitors which contain a pyridinone moiety as a central core structure.

SUMMARY OF THE INVENTION

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

The invention also includes the use of a compound of the invention, or a pharmaceutically acceptable salt thereof, in the manufacture of a medicament for inhibiting thrombus formation, preventing thrombus formation, inhibiting thrombin, inhibiting formation of fibrin, and inhibiting formation of blood platelet aggregates, in a mammal.

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl)carbodiimide hydrochloride |
| | Other |
| (BOC)$_2$O(BOC$_2$O) | di-t-butyl dicarbonate |
| n-Bu$_4$N+F- | tetrabutyl ammonium fluoride |
| nBuLi (n-Buli) | n-butyllithium |
| DMF | dimethylformamide |
| Et$_3$N (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylamine |
| | Amino Acid |
| Ile | Isoleucine |
| Phe | Phenylalanine |
| Pro | Proline |
| Ala | Alanine |
| Val | Valine |

DETAILED DESCRIPTION OF THE INVENTION AND PREFERRED EMBODIMENTS

Compounds of the invention are useful as thrombin inhibitors and have therapeutic value in for example, preventing coronary artery disease, and have the following structure:

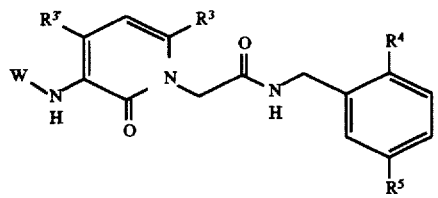

wherein
W is
  hydrogen,
  $R^1$—,
  $R^1OC(O)$—,
  $R^1C(O)$—,
  $R^1SO_2$—,
  $R^1NHSO_2$—,
  $(R^1)_2NSO_2$—,
  $R^1(CH_2)_nNHC(O)$—,
  $(R^1)_2CH(CH_2)_nNHC(O)$—, or wherein n is 0–4;
$R^1$ is
  $R^2(CH_2)_r$—, where r is 0–4, $(R^2)(OR^2)CH(CH_2)_p$—, where p is 1–4, $(R^2)_2CH(CH_2)_r$—, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7- membered mono- or bicyclic heterocyclic ring which can be saturated or unsaturated, and which contains from one to three heteroatoms selected from the group consisting of N, O and S, $R^2O(CH_2)_p$—, wherein p is 1–4, or $R^2(COOR^3)(CH_2)_r$—, where r is 1–4;

$R^2$ and $R^{14}$ are independently selected from

—phenyl, unsubstituted or substituted with one or more of $C_{1-4}$ alkyl, $C_{1-4}$ alkoxy, halogen, hydroxy, COOH, or $CONH_2$, naphthyl, biphenyl, a 5- to 7- membered mono- or a 9- to 10-membered bicyclic heterocyclic ring which can be saturated or unsaturated, and which contains from one to four heteroatoms selected from the group consisting of N, O and S, $C_{1-4}$ alkyl, $C_{3-7}$ cycloalkyl, $C_{7-12}$ bicyclic alkyl, or $C_{10-16}$ tricyclic alkyl;

$R^3$ and $R^{3'}$ are independently $C_{1-4}$ alkyl, $C_{3-7}$ cycloalkyl, or trifluoromethyl;

$R^4$ is hydrogen, $C_{1-4}$ alkyl, $C_{1-4}$ alkoxy, halogen,

—$OCH_2CF_3$,

—COOH,

—OH,

—$COOR^6$, where $R^6$ is $C_{1-4}$alkyl,

—$CONR^7R^8$, where $R^7$ and $R^8$ are independently hydrogen or $C_{1-4}$alkyl,

—$(C_2)_{1-4}OH$,

—$C_2NHC(O)C_3$,

—$C_2NHC(O)CF_3$,

—$C_2NHSO_2CH_3$,

—$SO_2NH_2$,

—$(C_2)_{1-4}SO_2NR^7R^8$,

—$(C_2)_{1-4}SO_2R^6$, a 5- to 7- membered mono- or a 9- to 10-membered bicyclic heterocyclic ring which can be saturated or unsaturated, and which contains from one to four heteroatoms selected from the group consisting of N, O and S,

—$XC_2CO_2H$,

—$XC_2CO_2C_3$,

—$XC_2CO_2(C_2)_{1-3}CH_3$,

—$X(CHR^9)_{1-3}C(O)NR^{10}R^{11}$, wherein $R^9$ is H or $C_{1-4}$ alkyl, $R^{10}$ and $R^{11}$ are independently hydrogen, $C_{3-7}$ cycloalkyl, aryl, heteroaryl, heterocycloalkyl, $C_{1-4}$ alkyl unsubstituted or substituted with one or more of hydroxy,

COOH, amino, dialkylamino, aryl, heteroaryl, or heterocycloalkyl, or $R^{10}$ and $R^{11}$ are joined to form a four to seven membered cycloalkyl ring unsubstituted or substituted with hydroxy, amino or aryl, or

—$XCH_2R^{14}$, wherein X is O, S or $CH_2$;

$R^5$ is hydrogen, halogen, $C_{1-4}$ alkyl, $C_{1-4}$ alkoxy,

CN, or $CO_2NH_2$, and pharmaceutically acceptable salts thereof.

In one class of compounds and pharmaceutically acceptable salts thereof, W is $R^1$ or $R^1SO_2$.

In a subclass of this class of compounds and pharmaceutically acceptable salts thereof, $R^1$ is $R^2(CH_2)_r$, or $(R^2)_2CH(CH_2)_r$, phenyl-$CH_2SO_2$, or diphenyl-$CHSO_2$.

In a group of this subclass of compounds and pharmaceutically acceptable salts thereof, $R^1$ is phenyl-$CH_2SO_2$, or diphenyl-$CHSO_2$.

In a subgroup of this group of compounds and pharmaceutically acceptable salts thereof, $R^3$ is $C_{1-4}$ alkyl.

In a family of this subgroup of compounds and pharmaceutically acceptable salts thereof, $R^3$ is methyl and $R^{3'}$ is hydrogen.

In a subfamily of this family of compounds and pharmaceutically acceptable salts thereof, $R^4$ is hydrogen, chlorine,

OH, $OCH_2CF_3$ $OCH_2C(O)NH_2$ $OCH_2C(O)NHCH_2CH_3$, or $OCH_2C(O)NH(CHCH_2CH_2)$; and $R^5$ is chlorine.

Specific embodiments of this subfamily include (note that the methyl group is conventionally indicated as a single bond attached to a ring):

-continued

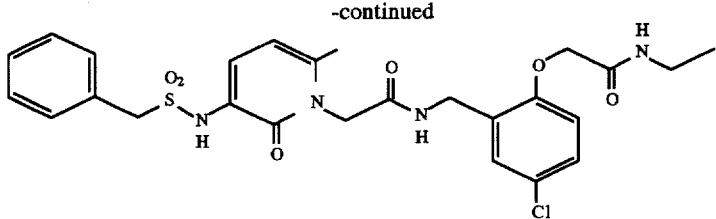

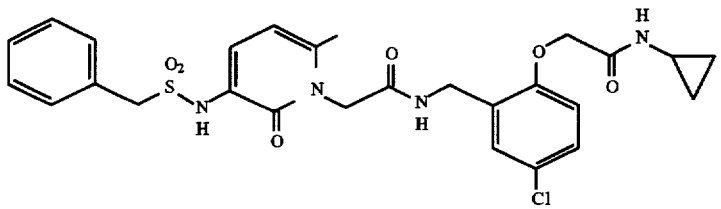

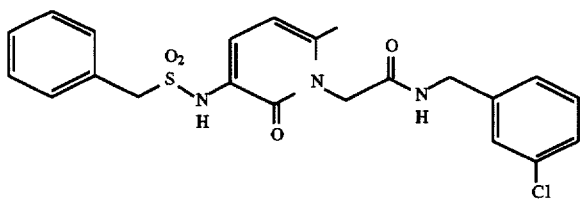

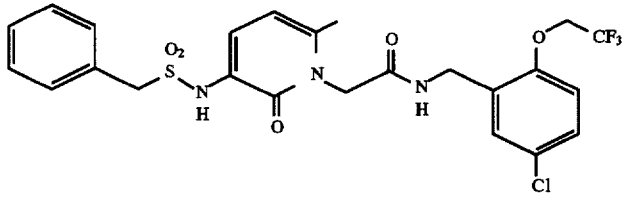

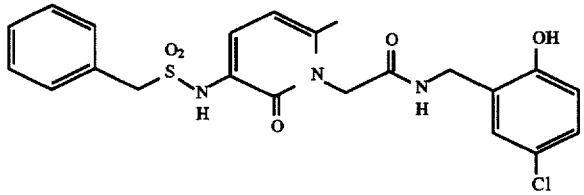

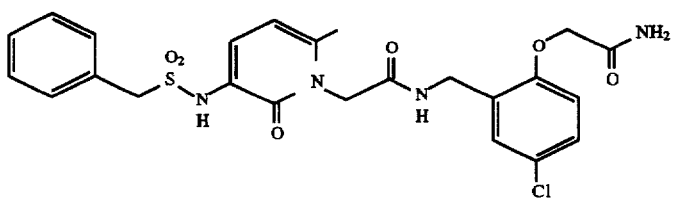

The compounds of the present invention, may have chiral centers and occur as racemates, racemic mixtures and as individual diastereomers, or enantiomers with all isomeric forms being included in the present invention. A racemate or racemic mixture does not imply a 50:50 mixture of stereoisomers.

When any variable occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl);

"alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like.

The term aryl as used herein except where noted, represents a stable 6- to 10-membered mono- or bicyclic ring system such as phenyl, or naphthyl. The aryl ring can be unsubstituted or substituted with one or more of $C_{1-4}$ lower alkyl; hydroxy; alkoxy; halogen; amino.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defmed heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.1 mg per kg of body weight per day (mg/kg/day) to about 100 mg/kg/day and preferably 1.0–100 mg/kg/day and most preferably 1–20 mg/kg/day. A suitably prepared medicament for once a day administration would thus contain between 9 mg and 9 g, preferably between 90 mg and 9 g, and most preferably between 90 mg and 1.8 g, e.g. 100 mg, 500 mg and 1 g. Advantageously, the thrombin inhibitors may be administered in divided doses of two, three, or four times daily. For such multiple administration, individual medicament strengths can be, for example, 25 mg, 33 mg or 50 mg,. Intravenously, the most preferred doses will range from about 0.01 to about 10 mg/kg/minute during a constant rate infusion. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-coagulation agents, including, but not limited to, fibrinogen receptor antagonists, heparin, aspirin, or warfarin, or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

METHODS OF MAKING

The following synthetic methods can be used to prepare the compounds of the present invention:

As exemplified by Example 1 (Scheme 1).

Starting 6-methyl-2-hydroxy-pyridine-3-carboxylic acid is reacted with diphenylphosphoryl azide (DPPA) and benzyl alcohol in Step A to afford the protected aminopyridine. This is alkylated in Step B with t-butylbromoacetate and the CBZ group is removed in Step C by hydrogenation over a catalyst. The resulting amine is then reacted with the appropriate reagent, in this case benzylsulfonyl chloride, in Step D with pyridine as an acid scavenger and the t-butyl ester is then removed under acidic conditions in Step E. The acid is then coupled in Step F with an amine, such as 2,5-dichlorobenzylamine, to afford the final product.

SCHEME 1

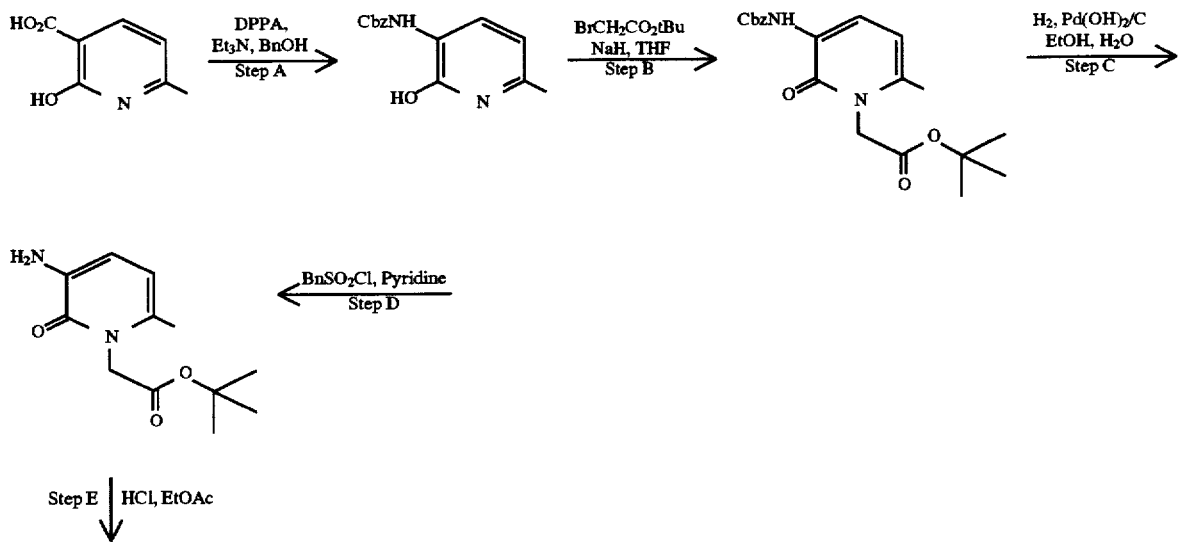

-continued
SCHEME 1

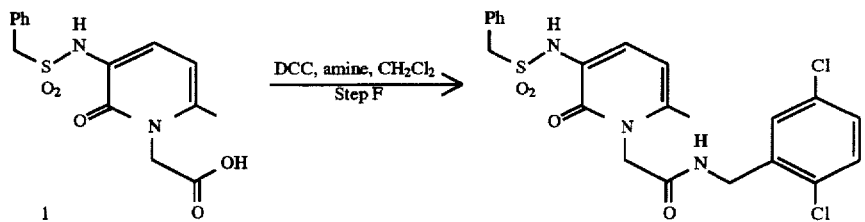

Amide couplings, e.g., Step F in Scheme 1, to form the compounds of this invention can be performed by the carbodiimide method with reagents such as dicyclohexylcarbodiimide, or 1-ethyl-3-(3-dimethyl-aminopropyl)carbodiimide. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice.

Modifications of the method will allow different W, $R^3$, $R^4$ and $R^5$ groups contemplated by the scope of the broad claim below to be present by the use of an appropriate reagent or appropriately substituted starting material in the indicated synthetic step. For example the starting pyridine in Step A, can have as the 6-substituent, ethyl, isopropyl, cyclopropyl, trifluoromethyl, and the like, to achieve the different operable values of $R^3$. Likewise, different W groups can be present by the use of an appropriate alkylating, carbonylating, sulfonylating, urealating agent, and the like, in Step D. Use of, for example, an alkyl halide, alkoxycarbonyl halide, acyl halide, alkylsulfonyl halide, or alkyl isocyanate will yield the corresponding values of W where W is $R^1$, $R^1OCO$, $R^1CO$, $R^1SO_2$, or $(R^1)_m(CH_2)_nNCO$. Likewise, an appropriate choice of the amine in Step F will allow the different operable values of $R^4$ and $R^5$ to be achieved. Obvious variations and modifications of the method to produce similar and obvious variants thereof, will be apparent to one skilled in the art.

A method for preparing compounds which contain, or are derivatives of, 2-hydroxybenzylamine as an end group is illustrated in Scheme 2 and is exemplified by Example 2.

4-Chlorosalicaldehyde is condensed with hydroxylamine hydrochloride in ethanolic aqueous sodium carbonate solution. The oxime is reduced by hydrogenation over a catalyst such as rhodium and the amine is protected as its BOC derivative under standard conditions. The phenol is alkylated in Step D with an acetate equivalent such as ethylbromoacetate and the resulting ester is hydrolysed with lithium hydroxide. The product carboxylic acid is coupled to an amine such as ethylaniine in Step F, and the BOC group is removed by strong acid. The amine is coupled to the product of Scheme 1, Step E to give the final product.

SCHEME 2

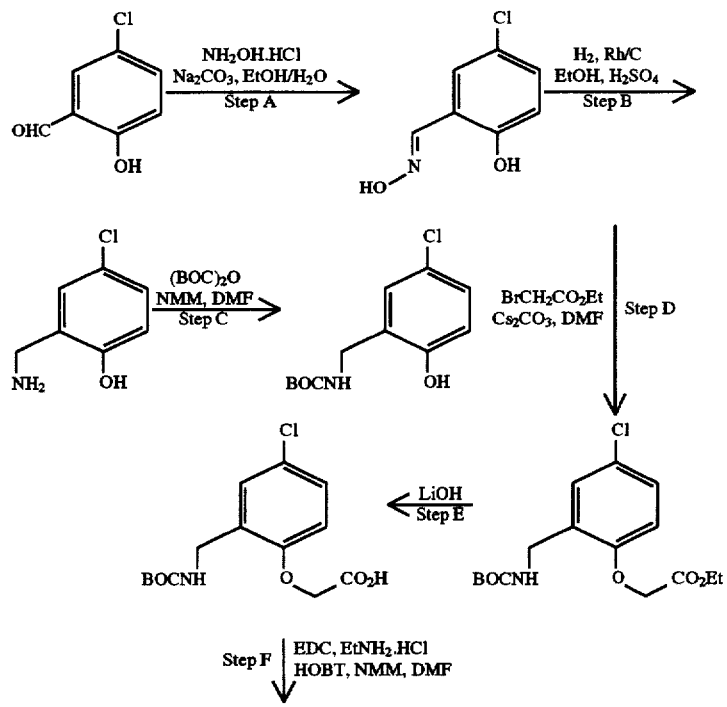

-continued
SCHEME 2

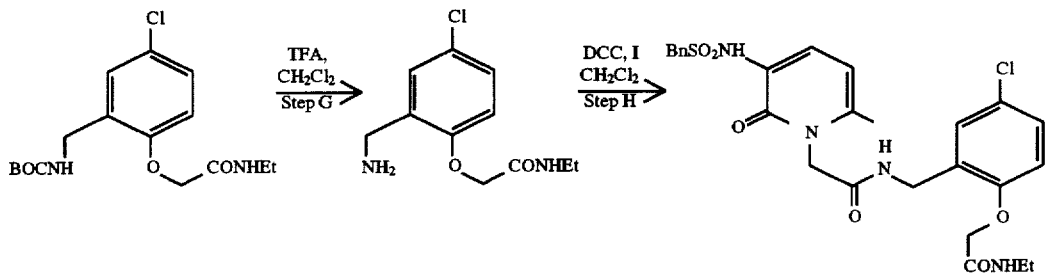

Modifications of this method will allow different $R^4$ and $R^5$ groups contemplated by the scope of the broad claim below to be present by the use of an appropriate reagent or appropriately substituted starting material in the indicated synthetic step. For example, appropriate choice of the amine in Step F will allow different values of $R^7$ and $R^8$ to be achieved. Obvious variations and modifications of the method to produce similar and obvious variants thereof, will be apparent to one skilled in the art.

A method for preparing compounds which are derivatives of 3-amino-4-trifluoromethyl-2-pyridinone is illustrated in Scheme 3. In Step A, 1,1,1, trifluoro-2,4-pentanedione is condensed with nitroacetamide in ethanolic diethylamine to give 2-hydroxy-6-methyl-3-nitro-4-trifluoromethylpyridine. This is alkylated in Step B with an acetate equivalent such as t-butyl bromoacetate in THF using sodium hydride as a base and the nitro group is reduced in Step C by hydrogenation using a catalyst such as palladium on carbon. The t-butyl group is removed in Step D by a strong acid such as HCl and the resulting carboxylic acid is coupled to ethyl-2-aminomethyl-4-chlorophenoxyacetamide in Step E to give the final product.

Modifications of the method will allow different $R^3$, $R^4$ and $R^5$ groups contemplated by the scope of the broad claim below to be present by the use of an appropriate reagent or appropriately substituted starting material in the indicated synthetic step. For example use of the appropriate dione in Step A will allow the different operable values of $R^3$ to be achieved. Similarly an appropriate choice of the amine in Step E will allow the different operable values of $R^4$ and $R^5$ to be achieved. Obvious variations and modifications of the method to produce similar and obvious variants thereof, will be apparent to one skilled in the art.

SCHEME 3

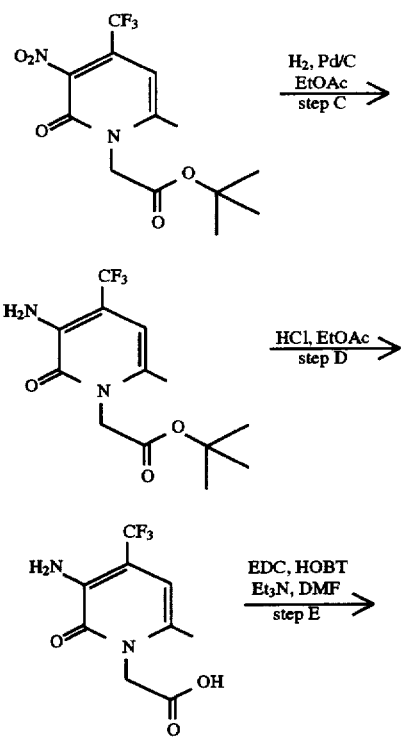

-continued
SCHEME 3

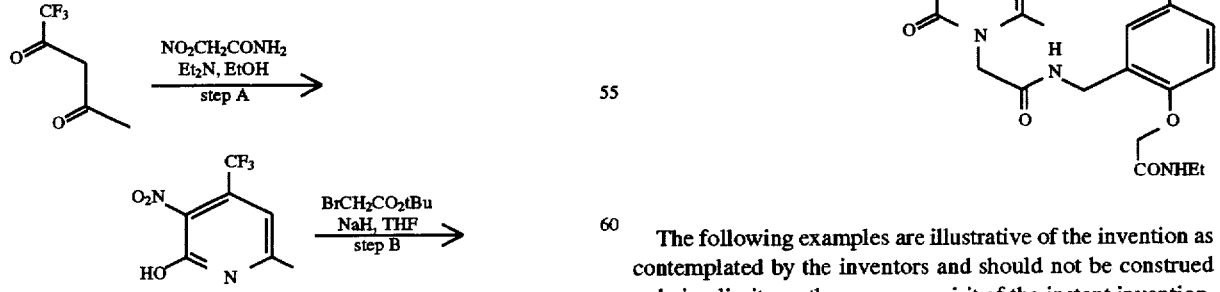

The following examples are illustrative of the invention as contemplated by the inventors and should not be construed as being limits on the scope or spirit of the instant invention.

EXAMPLE 1

Preparation of 3-Benzylsulfonylamino-6-methyl-1-(methylene-carboxamidomethyl-2,5-dichlorophenyl)-2-pyridinone

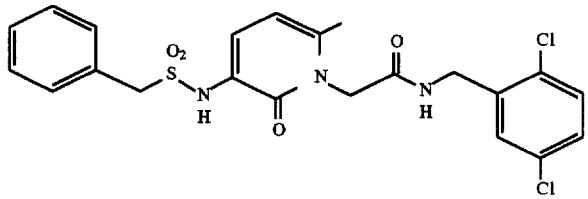

Step A: 3-Benzyloxvcarbonylamino-6-methyl-2-pyridinone

DPPA (35.6 ml, 165 mmol) was added to a stirred solution of 2-hydroxy-6-methylpyridine-3-carboxylic acid (22.97 g, 165 mmol) and triethylamine (23.0 ml, 165 mmol) in dry dioxane (300 ml) and the resulting solution was heated to reflux. After 16 h more triethylamine (23.0 ml, 165 mmol) and benzyl alcohol (17.1 ml, 165 mmol) were added and the solution was refluxed for a further 24 h. The reaction was concentrated in vacuo to remove most of the volatiles. The residue was partitioned between methylene chloride (500 ml) and brine (500 ml), acidified to pH 1 with 1M HCl (165 ml). The aqueous layer was extracted methylene chloride (two times) and the combined organic layers were washed with sodium hydrogen carbonate solution and brine, dried ($Na_2SO_4$) and evaporated in vacuo to a brown solid. This was recrystallized from methanol, to give the title compound as a tan solid:

$^1$H NMR (300 MHz, $CDCl_3$) δ2.29 (s, 3H, $CH_3$), 5.20 (s, 2H, $PhCH_2$), 6.06 (d,J=7.6 Hz, pyridinone-5-H), 7.32–7.43 (m, 5H, Ph), 7.67 (br s, 1H, CbzNH), 8.03 (br d, pyridinone-4-H).

Step B: 3-Benzyloxycarbonylamino-6-methyl-1-(t-butyl-methylenecarboxy)-2-pyridinone Sodium hydride (5.3 g, 0.22 mol) was added to a stirred slurry of 3-benzyloxycarbonylamino-6-methyl-2-pyridinone (53.2 g, 0.20 mol) at 0° C. t-Butylbromoacetate (45 ml, 0.27 mol) was added to the resulting solution and a precipitate rapidly forms. The reaction was warmed to rt over 1 h and after 2 h the solvent was evaporated in vacuo and the residue was partitioned between 1:1 water/brine (200 ml) and 6:1 THF/methylene chloride (700 ml). The organic layer was dried ($Na_2SO_4$) and evaporated in vacuo to a solid which was triturated with hexane to give the title compound as a crystalline solid:

$^1$H NMR (400 Mz, $CDCl_3$) δ1.47 (s, 9H), 2.25 (s, 3H), 4.75 (s, 2H), 5.19 (s, 2H), 6.09 (d,J=7.8 Hz), 7.30–7.40 (m, 5H), 7.75 (br s, 1H), 7.94 (br d, 1H).

Step C: 3-Amino-6-methyl-1-(t-butyl-methylenecarboxy)-2-pyridinone

A mixture of 3-benzyloxycarbonylamino-6-methyl-1-(t-butyl-methylenecarboxy)-2-pyridinone (5.59 g, 15.0 mmol) and Pearlman's catalyst (0.56 g) in 4:1 ethanol/water (200 ml) was shaken in a Parr apparatus under $H_2$ (50 psi) for 2 h. The reaction mixture was filtered through celite and evaporated in vacuo, azeotroping with ethanol to give the title compound as a solid:

$^1$H NMR (400 Mz, $CDCl_3$) δ1.46 (s, 9H, t-Bu), 2.18 (s, 3H, Me), 4.02 (br s, 2H, $NH_2$), 4.74 (s, 2H, $CH_2$), 5.90 (d,J=7.3 Hz, 1H, pyridinone H-5), 6.47 (d,J=7.3 Hz, 1H, pyridinone H-4).

Step D: 3-Benzylsulfonylamino-6-methyl-1-(t-butyl-methylenecarboxy)-2-pyridinone Benzylsulfonyl chloride (3.15 g, 16.5 mmol) was added to a stirred solution of 3-amino-6-methyl-1-(t-butyl-methylenecarboxy)-2-pyridinone (3.55 g, 14.9 mmol) in pyridine (30 ml) at 0° C. and as the resulting solution was stirred a thick precipitate formed. After 1 h the reaction mixture was evaporated in vacuo to a paste which was partitioned between methylene chloride and 10% potassium hydrogen sulfate solution. The organic layer was dried ($Na_2SO_4$) and evaporated in vacuo to give the title compound as a pale pink solid:

$^1$H NMR (400 Mz, $CDCl_3$) δ1.51 (s, 9H, t-Bu), 2.26 (s, 3H, Me), 4.31 (s, 2H, $PhCH_2$), 4.75 (s, 2H, $NCH_2$), 6.01 (d,J=7.7 Hz, 1H, pyridinone H-5), 7.22–7.34 (m, 7H, remaining H).

Step E: 3-Benzylsulfonylamino-6-methyl-1-methylenecarboxy-2-pyridinone

HCl gas was bubbled through a stirred suspension of 3-benzylsulfonylamino-6-methyl-1-(t-butyl-methylenecarboxy)-2-pyridinone (5.70 g, 14.52 mmol) in ethyl acetate (60 ml) at 0° C. until a solution had formed which was saturated with HCl. After 1.5 h at RT a thick suspension had formed. The mixture was degassed with nitrogen and filtered to give the title compound as a solid:

$^1$H NMR (400 Mz, $CD_3OD$) δ2.32 (s, 3H, Me), 4.43 (s, 2H, $PhCH_2$), 4.89 (s, 2H, $NCH_2$), 6.14 (d,J=7.7 Hz, 1H, pyridinone H-5), 7.28–7.33 (m, 6H, remaining H).

Step F: 3-Benzylsulfonylamino-6-methyl-1-(N-2,5-Dichloro benzyl-acetamido)-2-pyridinone EDC Hydrochloride (48 mg, 0.25 mmol) was added to a stirred mixture of 3-benzylsulfonylamino-6-methyl-1-methylenecarboxy-2-pyridinone (70 mg, 0.21 mmol), HOBT (34 mg, 0.25 mmol), 2,5-dichlorobenzylamine (44 mg, 0.25 mmol) and triethylamine (0.070 ml, 0.50 mmol) in DMF (2.5 ml) and the mixture was stirred for 16 h. The reaction was diluted with ethyl acetate and was washed with brine, dried ($Na_2SO_4$) and evaporated in vacuo to a solid. The crude product was purified by flash column chromatography on silica (50% ethylacetate/hexanes), to give the title compound as a crystalline solid:

$^1$H NMR (400 Mz, $CDCl_3$) δ2.43 (s, 3H, Me), 4.30 (s, 2H), 4.49 (d,J=6.1 Hz, 2H, $C_2N$), 4.68 (s, 2H), 6.05 (d,J=7.7 Hz, 1H), 7.16 (dt,=2.4 and 8.9 Hz, 1H), 7.24–7.40 (m, 8H); MS (FAB) 494 $(M+1)^+$.

EXAMPLE II

Preparation of 3-Benzylsulfonylamino-6-methyl1-[Ethyl-(2-methylenecarboxamidomethyl-4-chlorophenoxy)-acetamido]-2-pyridinone

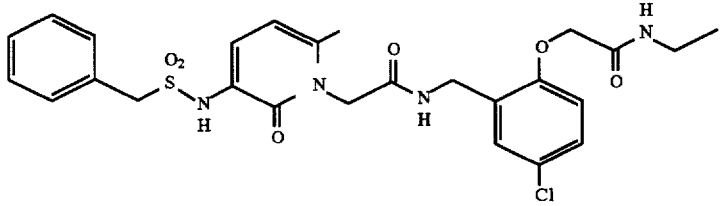

Step A: 4-Chlorosalicaldehyde Oxime

A solution of hydroxylamine hydrochloride (16.7 g, 0.24 mol) and sodium carbonate (12.7 g, 0.12 mol) in water (120 ml) was added to a stirred solution of 4-chlorosalicaldehyde (25.0 g, 0.16 mol) in ethanol (160 ml) and the resulting solution was heated to reflux. After 1 h the reaction was cooled, water (320 ml) was added and the resulting crystalline precipitate was isolated by filtration. A second crop was similarly collected and the combined solids were dried to give the title compound:

$^1$H NMR (400 Mz, CDCl$_3$) δ6.92 (d,J=8.8 Hz, 1H), 7.15 (d,J=2.6 Hz, 1H), 7.23 (dd,J=2.6 and 8.8 Hz, 1H), 7.26 (s, 1H), 8.16 (s, 1H), 9.71 (s, 1H).

Step B: 2-Hydroxy-5-Chlorobenzylamine

A mixture of 4-chlorosalicaldehyde oxime (10 g, 58.3 mmol) and 5% Rh/C (2.0 g) in ethanol (100 ml) containing concentrated sulfuric acid (10 ml) was shaken in a Parr apparatus under H$_2$ (60 psi) for 24 h. Water (100 ml) was added and the mixture was filtered through celite. The filtrate was concentrated until the product had crystallized out of solution. The solid was collected by filtration and the filtrate was further concentrated, adding water to give a second crop which was combined with the first to give after drying the title compound.

$^1$H NMR (400 Mz, CD$_3$OD) δ4.07 (s, 2H), 6.88 (d,J=8.6 Hz, 1H), 7.25 (dd,J=2.6 and 8.6 Hz, 1H), 7.31 (d,J=2.6 Hz, 1H).

Step C: N-t-Butoxycarbonyl-2-Hydroxy-5-Chlorobenzylamine

A mixture of 2-hydroxy-5-chlorobenzylamine (1.22 g, 4.77 mmol assuming the bisulfate salt), (BOC)$_2$O (1.56 g, 7.16 mmol) and N-methylmorpholine (1.05 ml, 9.54 mmol) in DMF (10 ml) was stirred for 5 h at r.t. The reaction was partitioned between water and ethyl acetate and the organic layer was washed with 5% KHSO$_4$ solution (2 times), sodium hydrogen carbonate solution and brine, dried (Na$_2$SO$_4$) and evaporated in vacuo to a solid. The crude product was recrystallized from ethyl acetate/hexanes (1:5, 12 ml) to give the title compound:

$^1$H NMR (400 Mz, CDCl$_3$) δ1.44 (s, 9H, t-Bu), 4.17 (d,J=6.8 Hz, 2H, C$_2$), 5.22 (br t, 1H, NH), 6.87 (d,J=8.6 Hz, 1H, H-3), 7.03 (d,J=2.6 Hz, 1H, H-6), 7.15 (dd,J=2.6 and 8.6 Hz, 1H, H-4).

Step D: Ethyl-(2-t-Butoxycarbonylaminomethyl-4-Chlorophenoxy)-Acetate

A mixture of N-t-butoxycarbonyl-2-hydroxy-5-chlorobenzylamine (730 mg, 2.83 mmol), Cs$_2$CO$_3$ (923 mg, 2.83 mmol) and ethylbromoacetate (0.314 ml, 2.83 mmol) on DMF (5 ml) was stirred for 2 h. The crude reaction mixture was partitioned between ethyl acetate and water and the organic layer was washed with brine, dried (Na$_2$SO$_4$) and evaporated in vacuo to an oil which was used for the next step.

Step E: 2-t-Butoxycarbonylaminomethyl-4-Chlorophenoxyacetic Acid

The product from Step D was suspended in 1:1:1 methanol/THF/water (9 ml) and lithium hydroxide hydrate (126 mg, 3.0 mmol) was added. After 16 h the volatiles were removed in vacuo and the solution was diluted with water and was washed with ethyl acetate, adding sufficient brine to disperse the emulsion. The aqueous layer was acidified with 5% KHSO$_4$ solution and was extracted with methylene chloride which was then dried (Na$_2$SO$_4$) and evaporated in vacuo to give the title compound as a solid:

$^1$H NMR (400 Mz, CDCl$_3$) δ1.44 (s, 9H, t-Bu), 4.35 (br s, 2H, NCH$_2$), 4.62 (s, 2H, OCH$_2$), 5.04 (br s, 1H, NH), 6.74 (d,J=7.9 Hz, 1H, H-3), 7.20 (d,J=2.6 Hz, 1H, H-6), 7.24 (d obscured, 1H, H-4).

Step F: Ethyl-(2-t-Butoxycarbonylaminomethyl-4-Chlorophenoxy)-Acetamide

EDC Hydrochloride (249 mg, 1.3 mmol) was added to a stirred mixture of 2-t-butoxycarbonylaminomethyl-4-chlorophenoxyacetic acid (316 mg, 1.0 mmol), HOBT (176 mg, 1.3 mmol), ethylamine hydrochloride (106 mg, 1.3 mmol) and N-methylmorpholine (0.396 ml, 3.6 mmol) in DMF (4 ml) and the mixture was stirred for 16 h. The reaction was partitioned between ethylacetate and 5% KHSO$_4$ solution and the organic layer was washed with 5% KHSO$_4$ solution, water, NaHCO$_3$ solution and brine, dried (Na$_2$SO$_4$) and evaporated in vacuo to a solid (333 mg) which was used for the next step.

Step G: Ethyl-(2-Aminomethyl-4-Chlorophenoxy)-Acetamide Ethyl-(2-t-butoxycarbonylaminomethyl-4-chlorophenoxy)-acetamide from Step F was dissolved in 2:1 methylene chloride/TFA (3 ml) and after 15 min the solvent was evaporated in vacuo. The residue was dissolved in water and the solution was washed with methylene chloride (twice). The aqueous layer was then basified with saturated sodium carbonate solution and NaCl was added to saturation. The mixture was extracted with ethyl acetate, and the organic layer was dried (Na$_2$SO$_4$) and evaporated in vacuo to give the title compound as a crystalline solid:

$^1$H NMR (300 MHz, CDCl$_3$) δ1.12 (t,J=7.3 Hz, 3H, Me), 1.54 (s, 9H, t-Bu), 3.31 (quintet,J=7.3 Hz, 2H, C$_2$Me), 3.90 (s, 2H, NCH$_2$), 4.58 (s, 2H, OCH$_2$), 6.80 (d,J=8.3 Hz, 1H, H-3), 7.19–7.23 (m, 2H, H-4, H-6), 8.01 (br s, 1H, CONH).

Step H: 3-Benzylsulfonylamino-6-methyl-1-[Ethyl-(2-Methylenecarboxamidomethyl -4-Chlorophenoxy)-Acetamide DCC (103 mg, 0.50 mmol) was added to a stirred solution of ethyl-(2-aminomethyl-4-chlorophenoxy)-acetamide (137 mg, 0.57 mmol) and 3-benzylsulfonylamino-6-methyl-1-methylenecarboxy-2-pyridinone (168 mg, 0.0.50 mmol) in methylene chloride (3 ml). After 3 h the resulting thick mixture was filtered through celite, washing the pad with a large volume of methylene chloride since the product is sparingly soluble, and the filtrate was evaporated in vacuo to a solid. The crude product was purified by flash column chromatography on silica (eluting with 3:1 hexanes/acetone followed by a methanol/chloroform gradient, 2–4% methanol) to give the title compound as a crystalline solid, m.p. 210°–213° C.:

$^1$H NMR (400 Mz, DMSO) δ0.98 (t,J=7.2 Hz, 3H, Me), 2.25 (s, 3H, Me), 3.11 (quintet,J=7.2 Hz, 2H, C$_2$Me), 4.40 (d,J=5.5 Hz, 2H, C$_2$NH), 4.49 (s, 2H), 4.50 (s, 2H), 4.79 (s, 2H), 6.09 (d,J=7.7 Hz, 1H), 6.94 (d,J=8.6 Hz, 1H), 7.12 (d,J=7.5 Hz, 1H), 7.26–7.33 (m, 7H), 8.02 (br t, 1H), 8.57 (s, 1H), 8.75 (br s, 1H); MS (FAB) 561 (M+1)$^+$.

Using the procedure of Example 2, the following compounds were prepared:

EXAMPLE 3

3-Benzylsulfonylamino-6-methyl-1-[cyclopropyl-(2-Methylenecarboxamidomethyl-4-Chlorophenoxy)-Acetamido]-2-Pyridinone

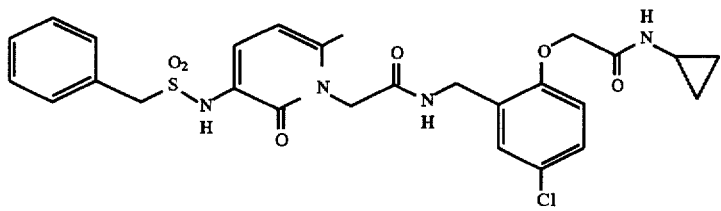

DCC (103 mg, 0.50 mmol) was added to a stirred solution of cyclopropyl-(2-aminomethyl-4-chlorophenoxy)-acetamide (127 mg, 0.50 mmol,) and 3-benzylsulfonylamino-6-methyl-1-methylenecarboxy-2-pyridinone (168 mg, 0.50 mmol) in methylene chloride (2 ml). After 16 h the resulting thick mixture was filtered through celite, washing through with 1:1 methanol/chloroform and the filtrate was evaporated in vacuo to a solid. The crude product was purified by flash column chromatography on silica (eluting with 3:1 hexanes/acetone followed by a methanol/chloroform gradient, 2–4% methanol) to give the title compound as a crystalline solid, m.p.>200° C.:

$^1$H MNR (400 Mz, CD$_3$OD) δ0.50–0.65 (m, 4H, C$_2$C$_2$), 2.29 (s, 3H, Me), 2.72 (m, 1H, CH), 4.41 (s, 2H), 4.48 (s, 2H), 4.49 (s, 2H), 4.81 (s, 2H), 6.15 (d,J=7.7 Hz, 1H), 6.90 (d,J=8.8 Hz, 1H), 7.24–7.35 (m, 8H); MS (FAB) 573 (M+1)$^+$.

EXAMPLE 4

3-Benzylsulfonylamino-6-methyl-1 -(2-Methylenecarboxamidomethyl-4-Chlorophenoxyacetamido)-2-Pyridinone

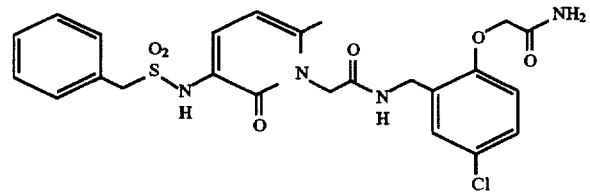

DCC (63 mg, 0.307 mmol) was added to a stirred solution of 2-aminomethyl-4-chlorophenoxyacetamide (101 mg, 0.307 mmol,) and 3-benzylsulfonylamino-6-methyl-1-methylenecarboxy-2-pyridinone (103 mg, 0.307 mmol) in methylene chloride (2 ml). After 66 h the resulting thick mixture was filtered through celite, washing through with 1:1 methanol/methylene chloride and the filtrate was evaporated in vacuo to a solid. The crude product was purified by flash column chromatography on silica (eluting with 3:1 hexanes/acetone followed by a methanol/chloroform gradient, 2–5% methanol) to give the title compound as a crystalline solid, m.p. >200° C.: $^1$H MNR (300 MHz, DMSO) δ2.48 (s, 3H, Me), 4.36 (d,J=5.9 Hz, 2 H, CH$_2$NH), 4.46 (s, 2H), 4.50 (s, 2H), 4.77 (s, 2H), 6.08 (d,J=7.6 Hz, 1H), 6.91 (d,J=8.6 Hz, 1H), 7.12 (d,J=7.6 Hz, 1H), 7.24–7.33 (m, 7H), 7.45 (br s, 2H, NH$_2$), 8.57 (s, 1H, SO$_2$NH), 8.71 (br t, 1H, CONH); MS (FAB) 533 (M+1)$^+$.

In addition, the following examples were prepared:

EXAMPLE 5

3-Benzylsulfonylamino-6-methyl-1-(2-Methylenecarboxamidomethyl-4-Chlorophenoxy)-2-Pyridinone

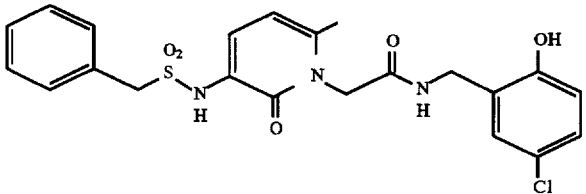

EDC Hydrochloride (236 mg, 1.23 mmol) was added to a stirred mixture of 3-benzylsulfonylamino-6-methyl-1-methylenecarboxy-2-pyridinone (415 mg, 1.23 mmol), HOBT (167 mg, 1.23 mmol), 2-hydroxy-5-chlorobenzylamine (195 mg, the product of Step B, Example B) and NMM (0.136 ml, 1.23 mmol) in DMF (1.2 ml) and the mixture was stirred for 3 h. The reaction was diluted with ethyl acetate and was washed with water, dried (Na$_2$SO$_4$) and evaporated in vacuo to a solid. The crude product was purified by flash column chromatography on silica (ethylacetate/hexanes/2% acetic acid gradient, 50–80% ethyl acetate), to give the title compound as a crystalline solid, m.p. >200° C.:

$^1$H MNR (400 Mz, CDCl$_3$) δ2.42 (s, 3H, Me), 4.22 (s, 2H), 4.26 (d, J=6.4 Hz, 2H, CH$_2$NH), 4.44 (s, 2H), 6.08 (d,J=7.7 Hz, 1H), 6.72 (d, J=8.6 Hz, 1H), 7.01–7.15 (m, 7H), 7.43 (d,J=7.7 Hz, 1H), 8.01 (br t, 1H, CONH); MS (FAB) 476 (M+1)$^+$.

EXAMPLE 6

3-Benzylsulfonylamino-6-methyl-1-[2,2,2-Trifluoroethyl-(2-Methylenecarboxamidomethyl-4-Chloro)-phenoxy]-2-Pyridinone

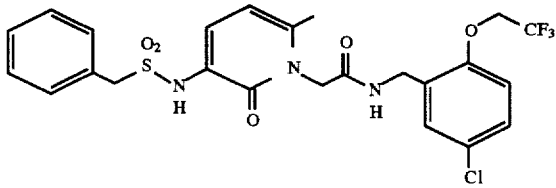

DCC (25 mg, 0.12 mmuol) was added to a stirred solution of 2-(2,2,2-trifluoroethyl)-5-chlorobenzylarnine (29 mg, 0.12 mmol,) and 3-benzylsulfonylamino-6-methyl-1-methylenecarboxy-2-pyridinone (61 mg, 0.18 mmol) in methylene chloride (0.7 ml). After 16 h the resulting thick mixture was filtered through celite, washing with methylene chloride and the filtrate was evaporated in vacuo to a solid. The crude product was purified by flash column chromatography on silica (eluting with 3:1 hexanes/acetone followed by 50% ethyl acetate/hexanes) to give a crystalline solid which was triturated with methylene chloride to give the title compound as a crystalline solid, m.p. >200° C.:

$^1$H MNR (300 MHz, DMSO) δ2.26 (s, 3H, Me), 4.28 (d,J=5.6 Hz, 2H, CH$_2$NH), 4.51 (s, 2H), 4.75–4.83 (m, 4H), 6.09 (d,J=7.6 Hz, 1H), 7.01–7.31 (m, 9H), 8.56 (br s, 1H, SO$_2$NH), 8.70 (br t, 1H, CONH); MS (FAB) 598 (M+1)$^+$.

EXAMPLE 7

3-Benzylsulfonylamino-6-methyl-1-(Methylenecarboxamidomethyl-3-Chloropheny)-2-Pyridinone

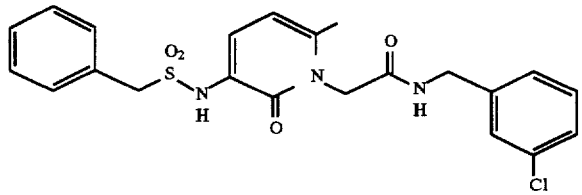

DCC (43 mg, 0.21 mmol) was added to a stirred solution of 3-chlorobenzylamine (0.025 ml, 0.21 mmol,) and 3-benzylsulfonylamino-6-methyl-1-methylenecarboxy-2-pyridinone (70 mg, 0.21 mmol) in methylene chloride (1.0 ml). After 16 h the resulting thick mixture was filtered through celite, washing with methylene chloride and the filtrate was evaporated in vacuo to a solid. The crude product was purified by flash column chromatography on silica (eluting with 3:1 hexanes/acetone followed by an ethyl acetate/hexanes gradient, 60–100% ethyl acetate) to give a crystalline solid which was triturated with methanol to give the title compound as a solid, m.p. 176°–178° C.:

$^1$H MNR (400 Mz, CDCl$_3$, 1 drop CD$_3$OD) δ2.41 (s, 3H, Me), 4.31 (s, 2H), 4.41 (s, 2H), 4.67 (s, 2H), 6.08 (d,J=7.6 Hz, 1H), 7.15–7.34 (m, 1OH); MS (FAB) 460 (M+I)$^+$.

EXAMPLE 8

In Vitro Assay for Determining Proteinase Inhibition

Assays of human a-thrombin and human trypsin were performed by the methods substantially as described in *Thrombosis Research*, Issue No. 70, page 173 (1993) by S. D. Lewis et al.

The assays were carried out at 25° C. in 0.05M TRIS buffer pH 7.4, 0.15M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used to measure (at 405 nm) the time dependent appearance of p-nitroaniline. sar-PR-pna was used to assay human α-thrombin (K$_m$=125 μM) and bovine trypsin (K$_m$=125 μM). p-Nitroanilide substrate concentration was determined from measurements of absorbance at 342 nm using an extinction coefficient of 8270 cm$^{-1}$M$^{+1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate Z-GPR-afc (K$_m$=27 μM) was determined from the increase in fluorescence at 500 nm (excitation at 400 nM) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in equation 1.

$$V_o/V_i = 1 + [I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The inhibitory activity of each of the following compounds against human thrombin, represented by Ki, is less than 15 nM. These are selective compounds, as evidenced by their inhibitory activity against human trypsin (represented by Ki), which is at least 1800 nM.

TABLE 1

[Structure: benzylsulfonylamino-pyridinone-acetamide-chlorophenyl with R substituent]

| R |
|---|
| H |
| Cl |
| OH |
| OCH₂CONHEt |
| OCH₂CONHC₃H₅ |
| OCH₂CONH₂ |
| OCH₂CF₃ |

EXAMPLE 9

In Vivo Studies To Measure Thrombotic Occlusions

Applicants have conducted in vivo studies of the compounds claimed herein using the following rat ferric chloride assay substantially as described in *Thrombosis Research*, No. 60, page 269(1990) by Kurtz et al.

In the assay used to determine in vivo activity of the thrombin inhibitors or the invention, Male Sprague-Dawley rats (body weights 200–350 grams) were anesthetized with dial-urethane solution (0.1 ml/100 gm body weight i.p.), and a lateral tail vein was cannulated with a 23 gauge needle connected to a 12 inch length of PE50 tubing. The tubing was attached to a 3-way valve by a tubing adapter. Saline (control) or test compound, as appropriate, was administered via the tail vein catheter. A tracheostomy was performed with a 0.75 inch length of PE205 tubing. The right carotid artery was exposed and a 1.3 mm diameter Doppler flow probe was placed on the vessel. Body temperature was maintained at 37° C. using a heat lamp.

Rats (8–10/group) were randomized to continuous intravenous infusions of saline or test compound administered via the tail vein at a rate of 0.028 ml/min. Treatment infusions were initiated 60 min before the placement of a 3 mm square piece of Whatman No. 1 filter paper saturated with 35% FeCl₃ onto the exposed carotid artery distal to the flow probe. Treatment infusions were continued for an additional 90 minutes after the application of FeCl₃ (total infusion duration 150 minutes) if thrombotic occlusions did not occur, or were terminated 30 minutes after thrombotic occlusion of the vessel. Time to occlusion was defined as the time from application of FeCl3 to thrombotic occlusion of the vessel. At the termination of the study (90 minutes after application of FeCl₃ in animals which did not occlude, or at 30 minutes after thrombotic occlusion), 3 ml blood samples were drawn by cardiac puncture into 0.3 ml of 3.8% sodium citrate.

The results show that the compounds of the invention are effective in preventing thrombotic occlusions.

EXAMPLE 10

Tablet Preparation

Tablets containing 25.0, 50.0, and 100.0 mg., respectively, of the following active compounds are prepared as illustrated below:

3-Benzylsulfonylamino-6-methyl-1-(methylenecarboxamidomethyl-2,5-dichlorophenyl)-2-pyridinone.

3-Benzylsulfonylamino-6-methyl-1-[Ethyl-(2-methylenecarboxamidomethyl-4-chlorophenoxy)-acetamido]-2-pyridinone.

3-Benzylsulfonylamino-6-methyl-1-[cyclopropyl-(2-Methylenecarboxamidomethyl-4-Chlorophenoxy)-Acetamido]-2-Pyridinone.

3-Benzylsulfonylamino-6-methyl-1-(2-Methylenecarboxamidomethyl-4-Chlorophenoxyacetamido)-2-Pyridinone

| TABLE FOR DOSES CONTAINING FROM 25-100 MG OF THE ACTIVE COMPOUND | | | |
|---|---|---|---|
| | Amount-mg | | |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

What is claimed is:

1. A compound having the formula:

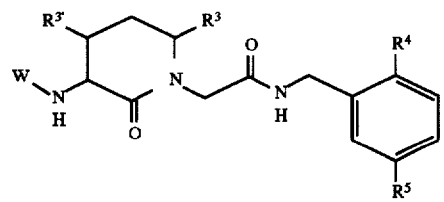

wherein
W is
  hydrogen,
  R¹—,
  R¹OC(O)—,
  R¹C(O)—,
  R¹SO₂—,
  R¹ NHSO₂—,
  (R¹)₂NSO₂—,
  R¹ (CH₂)ₙNHC(O)—,
  (R¹)₂CH(CH₂)ₙNHC(O)—, or wherein n is 0–4;
R¹ is
  R²(CH₂)ᵣ—, where r is 0–4,
  (R²)(OR²)CH(CH₂)ₚ—, where p is 1–4,
  (R²)₂CH(CH₂)ᵣ—, where r is 0–4 and each R² can be the same or different, and wherein (R²)₂ can also form a ring with CH represented by C₃₋₇ cycloalkyl, C₇₋₁₂ bicylic alkyl, or C₁₀₋₁₆ tricylic alkyl,
  R²O(CH₂)ₚ—, wherein p is 1–4, or $R^2(COOR^3)(CH_2)_r$—, where r is 1-4;

$R^2$ and $R^{14}$ are independently selected from
— phenyl, unsubstituted or substituted with one or more of $C_{1-4}$ alkyl, $C_{1-4}$ alkoxy, halogen, hydroxy, COOH, or $CONH_2$,
naphthyl,
biphenyl,
$C_{1-4}$ alkyl,
$C_{3-7}$ cycloalkyl,
$C_{7-12}$ bicyclic alkyl, or
$C_{10-16}$ tricyclic alkyl;

$R^3$ is
$C_{1-4}$ alkyl,
$C_{3-7}$ cycloalkyl, or
trifluoromethyl;

$R^{3'}$ is
hydrogen,
$C_{1-4}$ alkyl,
$C_{3-7}$ cycloalkyl, or
trifluoromethyl;

$R^4$ is
hydrogen,
$C_{1-4}$ alkyl,
$C_{1-4}$ alkoxy,
halogen,
—$OCH_2CF_3$,
—COOH,
—OH,
—$COOR^6$, where $R^6$ is $C_{1-4}$ alkyl,
—$CONR^7R^8$, where $R^7$ and $R^8$ are independently hydrogen or $C_{1-4}$ alkyl,
—$(CH_2)_{1-4}OH$,
—$CH_2NHC(O)CH_3$,
—$CH_2NHC(O)CF_3$,
—$CH_2NHSO_2CH_3$,
—$SO_2NH_2$,
—$(CH_2)_{1-4}SO_2NR^7R^8$,
—$(CH_2)_{1-4}SO_2R^6$,
—$XCH_2CO_2H$,
—$XCH_2CO_2CH_3$,
—$XCH_2CO_2(CH_2)_{1-3}CH_3$,
—$X(CHR^9)_{1-3}C(O)NR^{10}R^{11}$,
wherein
$R^9$ is H or $CH_{1-4}$ alkyl,
$R^{10}$ and $R^{11}$ are independently
hydrogen,
$C_{3-7}$ cycloalkyl,
aryl,
heteroaryl,
heterocycloalkyl,
$C_{1-4}$ alkyl unsubstituted or substituted with one or more of hydroxy,
COOH,
amino,
dialkylamino,
aryl,
heteroaryl, or
heterocycloalkyl, or
$R^{10}$ and $R^{11}$ are joined to form a four to seven membered cycloalkyl ring unsubstituted or substituted with hydroxy, amino or aryl, or
—$XCH_2R^{14}$,
wherein X is O, S or $CH_2$;

$R^5$ is
hydrogen,
halogen,
$C_{1-4}$ alkyl,
$C_{1-4}$ alkoxy,
CN, or
$CO_2NH_2$, and pharmaceutically acceptable salts thereof.

2. A compound of claim 1, and pharmaceutically acceptable salts thereof, wherein W is $R^1$ or $R^1SO_2$.

3. A compound of claim 2, and pharmaceutically acceptable salts thereof, wherein $R^1$ is $R^2(CH_2)_r$, or $(R^2)_2CH(CH_2)_r$, phenyl-$CH_2SO_2$, or diphenyl-$CHSO_2$.

4. A compound of claim 3, and pharmaceutically acceptable salts thereof, wherein $R^1$ is phenyl-$CH_2SO_2$, or diphenyl-$CHSO_2$.

5. A compound of claim 4, and pharmaceutically acceptable salts thereof, wherein $R^3$ is $C_{1-4}$ alkyl.

6. A compound of claim 5, and pharmaceutically acceptable salts thereof, wherein $R^3$ is methyl and $R^{3'}$ is hydrogen.

7. A compound of claim 6, and pharmaceutically acceptable salts thereof, wherein $R^4$ is
hydrogen,
chlorine,
OH,
$OCH_2CF_3$
$OCH_2C(O)NH_2$
$OCH_2C(O)NHCH_2CH_3$, or
$OCH_2C(O)NH(CHCH_2CH_2)$; and $R^5$ is chlorine.

8. The compound of claim 7, and pharmaceutically acceptable salts thereof, selected from:

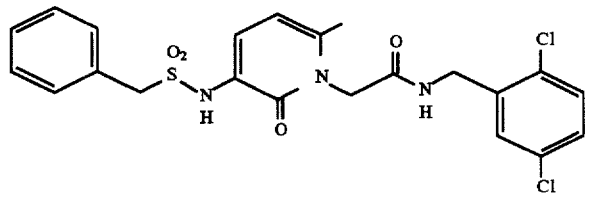

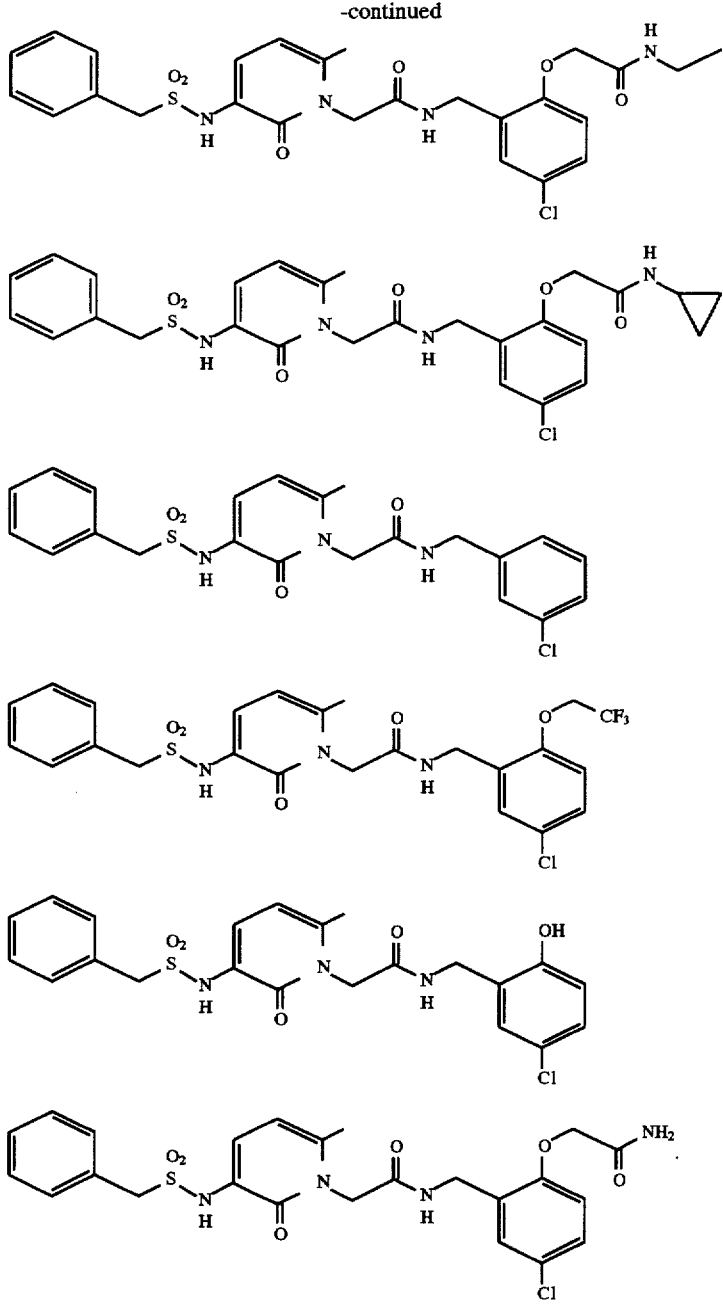

9. A pharmaceutical composition for inhibiting thrombin in blood comprising an effective amount of a compound of claim 1 and a pharmaceutically acceptable carrier.

10. A pharmaceutical composition for inhibiting formation of blood platelet aggregates in blood comprising an effective amount of a compound of claim 1 and a pharmaceutically acceptable carrier.

11. A pharmaceutical composition for inhibiting thrombus formation in blood comprising an effective amount of a compound of claim 1 and a pharmaceutically acceptable carrier.

12. A method for inhibiting thrombin in blood comprising administering to a mammal in need of said treatment an effective amount of a composition of claim 7.

13. A method for inhibiting formation of blood platelet aggregates in blood comprising administering to a mammal in need of said treatment an effective amount of a composition of claim 7.

14. A method for inhibiting thrombus formation in blood comprising administering to a mammal in need of said treatment an effective amount of a composition of claim 7.

15. A method for inhibiting thrombus formation in blood comprising administering to a mammal in need of said treatment an effective amount of a compound of claim 1 with a fibrinogen receptor antagonist.

* * * * *